(12) United States Patent  (10) Patent No.: US 7,117,551 B1
Dinkler, II et al.  (45) Date of Patent: Oct. 10, 2006

(54) HEAD SUPPORT SYSTEM

(75) Inventors: Charles E. Dinkler, II, Cincinnati, OH (US); Kevin R. Easton, Cincinnati, OH (US)

(73) Assignee: Integra Ohio, Inc., Cincinnati, OH (US)

( * ) Notice: Subject to any disclaimer, the term of this patent is extended or adjusted under 35 U.S.C. 154(b) by 21 days.

(21) Appl. No.: 11/001,524

(22) Filed: Dec. 1, 2004

Related U.S. Application Data

(60) Provisional application No. 60/526,047, filed on Dec. 1, 2003, provisional application No. 60/544,863, filed on Feb. 13, 2004.

(51) Int. Cl.
*A61G 13/12* (2006.01)
(52) U.S. Cl. .................. 5/637; 5/622; 5/640; 5/643
(58) Field of Classification Search ............... 5/622, 5/637, 640, 643; 297/405–410
See application file for complete search history.

(56) References Cited

U.S. PATENT DOCUMENTS

| | | | |
|---|---|---|---|
| 3,099,441 A * | 7/1963 | Ries ........................... | 5/637 |
| 3,936,641 A * | 2/1976 | Heimur ...................... | 5/637 |
| 4,108,426 A | 8/1978 | Lindstroem et al. | |
| 4,169,478 A | 10/1979 | Hickmann | |
| 4,360,028 A | 11/1982 | Barbier et al. | |
| 4,545,572 A | 10/1985 | Day | |
| 4,620,697 A * | 11/1986 | Pithon ........................ | 5/640 |
| 5,147,287 A | 9/1992 | Jewell et al. | |
| 5,214,815 A | 6/1993 | Agbodoe et al. | |
| 5,269,034 A | 12/1993 | Day et al. | |
| 5,276,927 A | 1/1994 | Day | |
| 5,537,704 A | 7/1996 | Dinkler | |
| 5,560,728 A * | 10/1996 | McFadden ................ | 403/53 |
| 5,564,663 A | 10/1996 | Cook et al. | |
| 6,117,143 A | 9/2000 | Hynes et al. | |
| 6,179,846 B1 | 1/2001 | McFadden et al. | |
| 6,315,783 B1 | 11/2001 | Katz et al. | |
| 6,594,839 B1 * | 7/2003 | Papay ........................ | 5/637 |
| 6,629,982 B1 | 10/2003 | Day et al. | |
| 6,684,428 B1 | 2/2004 | Grotenhuis et al. | |
| 6,770,082 B1 | 8/2004 | Dominguez et al. | |

* cited by examiner

*Primary Examiner*—Michael Trettel
(74) *Attorney, Agent, or Firm*—Wood, Herron & Evans, L.L.P.

(57) ABSTRACT

A head support system for use with a patient support. The head support system has a support structure with a crossbar extending transverse to, and connected to, the patient support. A head support device is removably mountable to a portion of the support structure exclusive of the crossbar and provides a static support for the patient's head. A head stabilization device is removably mountable to the crossbar of the support structure and stabilizes the patient's head.

21 Claims, 8 Drawing Sheets

HEAD SUPPORT SYSTEM

This application claims the benefit of U.S. Provisional Application No. 60/526,047, filed on Dec. 1, 2003 and U.S. Provisional Application No. 60/544,863, filed on Feb. 13, 2004, all of which are hereby expressly incorporated by reference herein

FIELD OF THE INVENTION

This invention relates to surgical equipment and more particularly, a head support system.

BACKGROUND OF THE INVENTION

During surgical procedures, one or more devices may be used to support a patient's head. For example, there may be a need to provide a static support for a patient's head; and typically, a static head support includes one or more pads that provide a static subjacent support of the patient's head in a prone or supine position. Such a static head support is mounted on a crossbar that extends transversely off the end of a patient support such as an operating table. Alternatively, a stabilization device, such as a skull clamp, is also used to support and stabilize a patient's head, and such a skull clamp is also mounted on the crossbar. In some applications, both static head support and skull clamp stabilization are desired, and then both devices must be mounted on the crossbar. In those situations where both subjacent support and lateral stabilization are required, having to mount both devices from the same crossbar member is complicated, inflexible and inconvenient. Therefore, there is a need to provide a support structure for a head support and a stabilization device that is more convenient and flexible to use.

In the process of supporting or stabilizing the patient's head, surgical draping is applied in a known manner to the patient and portions of the structure supporting the head support or stabilization device. Depending on the surgery being performed, it may be required to lower the head support out of contact with the patient's head and subsequently, raise the head support back into contact with the patient's head. Known head supports often use a pawl pin or locking screw to control elevation, and such pawl pin or locking screw are centrally located and difficult to reach beneath the surgical draping. Further, any adjustments in elevation require two hands, one to operate the pawl or screw and one to lift or lower the head support. As can be appreciated, the presence of the draping makes such adjustments more difficult, time consuming and a distraction from the surgical procedure. Therefore, there is a need for a head support that can be easily adjusted and locked in a desired elevation with a minimum of disturbance to the surgical draping and a minimum of distraction from the surgical procedure being performed.

Therefore, there is a need to provide structure for more flexibly mounting head support and stabilization devices.

SUMMARY OF THE INVENTION

The present invention provides head support systems that are highly flexible and can be used with a wide range of imaging, neuro-navigational and surgical procedures. The head support systems of the present invention provide both static head support, for example, a horseshoe pad, other pads, pins, etc., and head stabilization, for example, a skull clamp or other devices. The head support systems of the present invention permit a head support to be adjusted and simultaneously locked at any elevation with a motion of only one hand. Further, the components of the head support systems of the present invention are easily disassembled for ease of cleaning. Such a combination of static load support and stabilization is especially useful when working with pediatric patients and in plastic surgery.

In accordance with the principles of the present invention and in accordance with the described embodiments, the present invention provides a head support system for use with a patient support, which provides support and stabilization for a patient's head. The head support system has a support structure with a crossbar extending transverse to, and connected to, the patient support. A head support is removably mountable to a portion of the support structure exclusive of the crossbar and provides a static support for the patient's head. A head stabilization device is removably mountable to the crossbar of the support structure and stabilizes the patient's head.

In a further embodiment of the invention, the head support system has a gear box mounted on the support structure. The gear box is connected to the head support; and a crank rod operates the gear box to move the head support to, and simultaneously lock the head support at, a desired vertical position. A gear rack is connected to the gear box, and a ball-and-socket joint connects the head support to the gear rack, thereby permitting the head support to pivot with respect to the gear rack.

These and other objects and advantages of the present invention will become more readily apparent during the following detailed description taken in conjunction with the drawings herein.

DETAILED DESCRIPTION OF THE INVENTION

Figure 1:
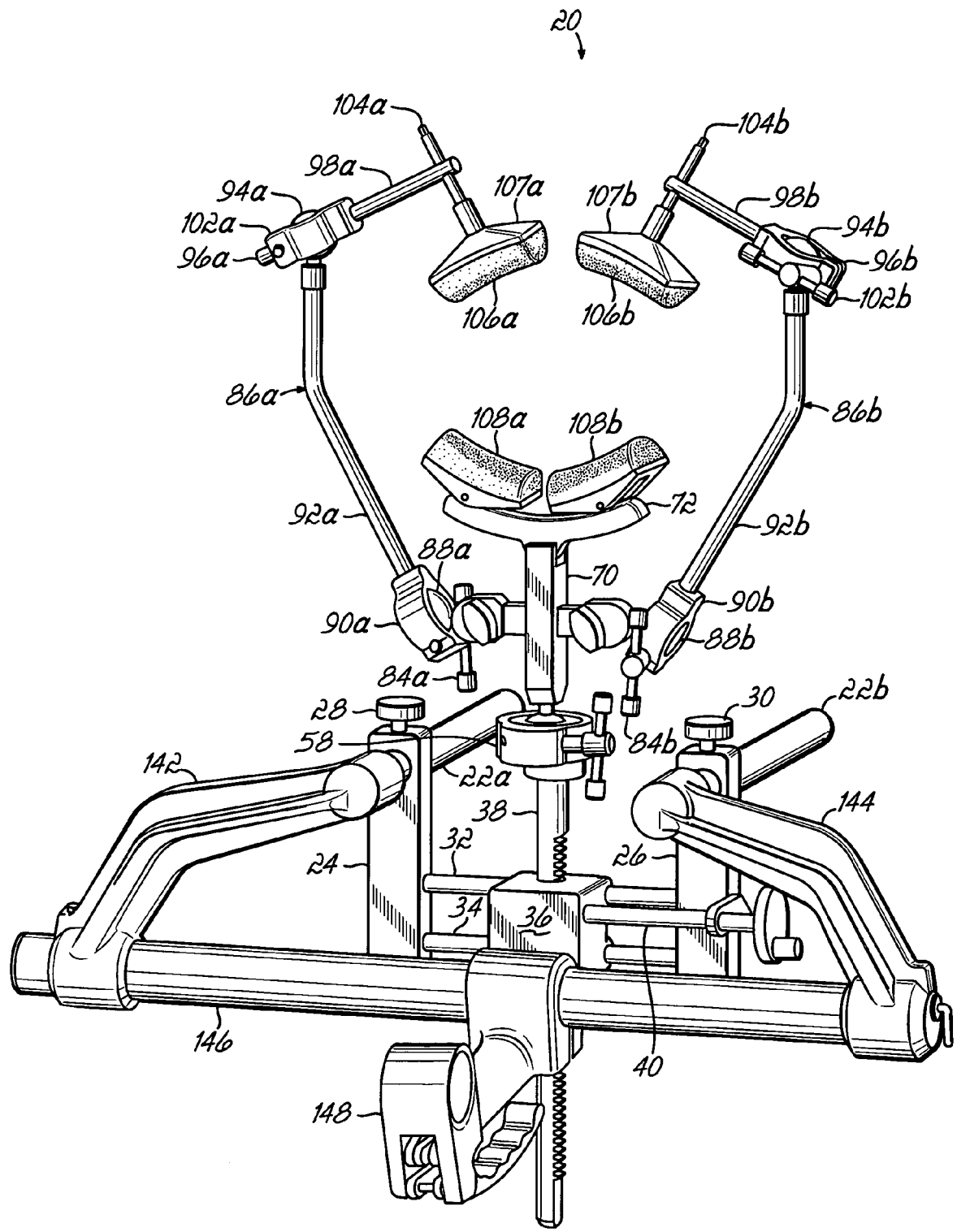
FIG. 1 is a perspective view of a first embodiment of a head support system in accordance with the principles of the present invention.
Figure 2:
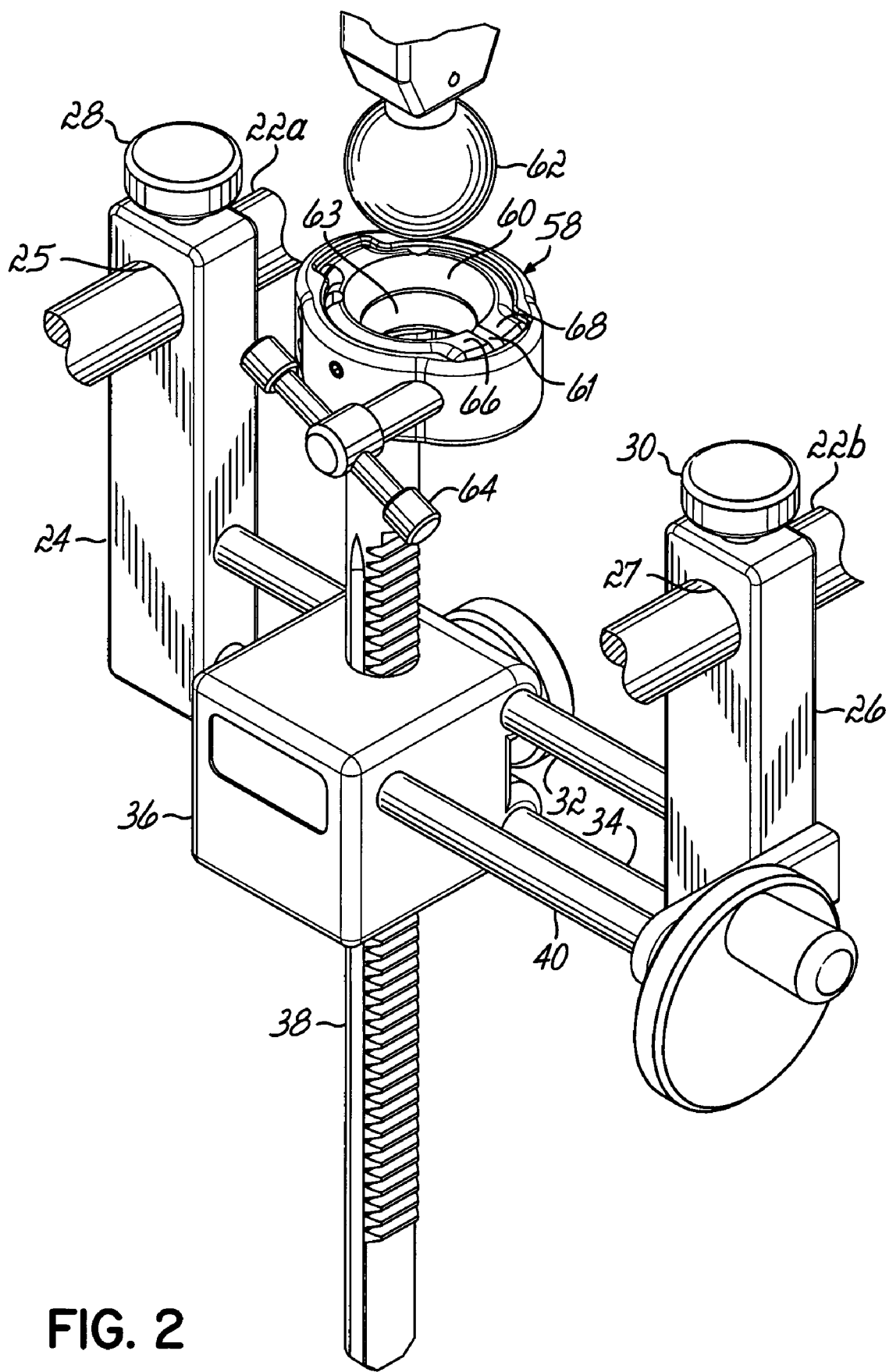
FIG. 2 is a perspective view of a lower portion of the head support system shown in FIG. 1, which is suspended from supported shafts.

Referring to FIGS. 1 and 2, in a first embodiment, a head support system 20 is mounted on spaced-apart support shafts 22a, 22b that are connected to an end of a patient support (not shown), for example, an operating table in a known manner. The support shafts 22a, 22b extend substantially parallel with a length of the patient support. First and second support posts 24, 26 have respective bores 25, 27 that receive respective support shafts 22a, 22b, and the support posts 24, 26 can be locked at a desired position by means of respective locking screws 28, 30. Upper and lower guide rods 32, 34 have first ends fixed in a lower portion of the first support post 24. Opposite ends of the guide rods 32, 34 are supported in a lower portion of the second support post 26. The guide rods 32, 34 extend through a gear box housing 36, and thus, the housing 36 is slidable longitudinally along the guide rods 32, 34 but cannot rotate with respect thereto. Also extending through the housing 36 is a gear rack 38 which is used to raise and lower a head support device, for example, pads 108a, 108b, by rotating the crank rod 40. The crank rod 40 is supported by a bracket 41 rigidly connected to the support post 26.

Figure 3:
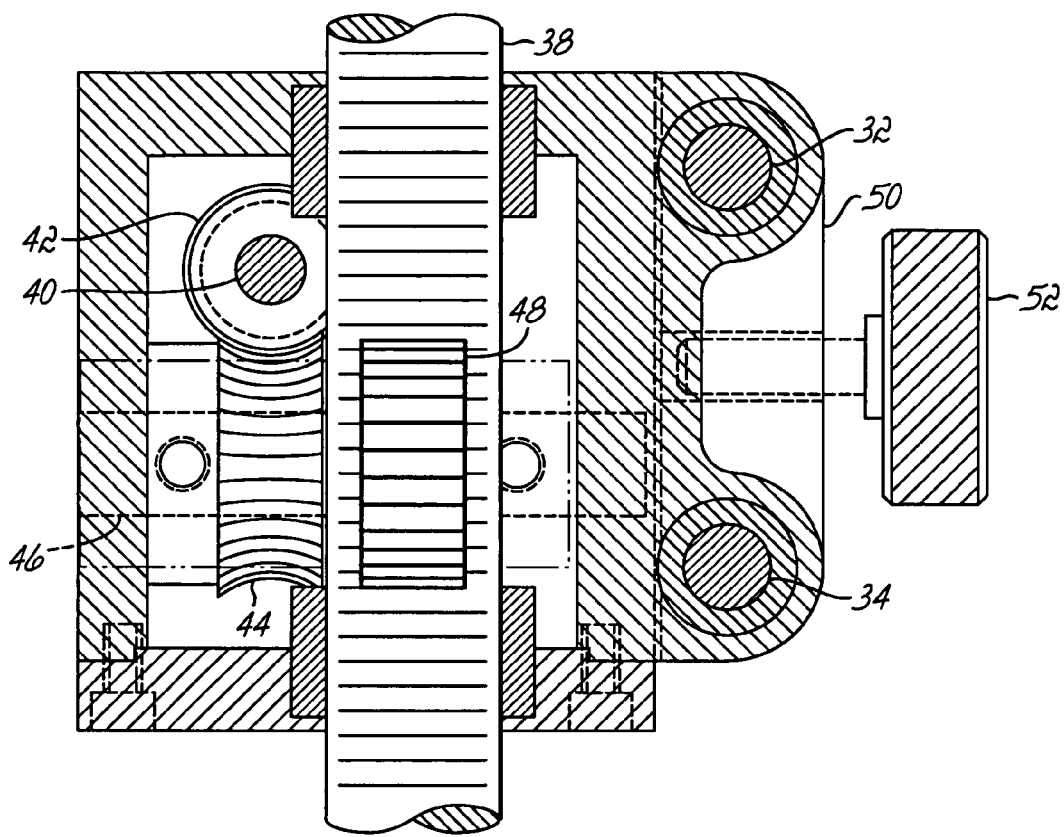
FIG. 3 is a schematic side elevation view of several interior components of a gear box used with the head support system of FIG. 1.
Figure 4:
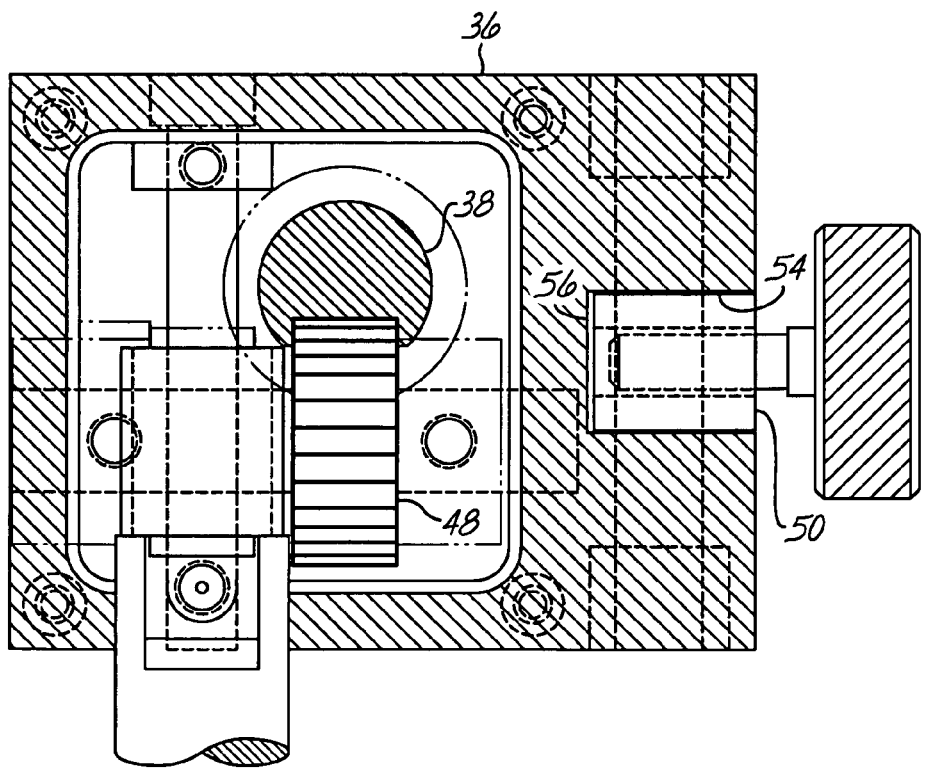
FIG. 4 is a schematic top view of locking components of the gear box used with the head support system of FIG. 1.

Referring to FIG. 3, within the gear box 36 a worm 42 is mounted on an end of the crank rod 40. The worm 42 meshes with worm gear 44 that is fixed on a shaft 46 that, in turn, also carries a spur gear 48. The spur gear 48 meshes with the gear rack 38. Thus, rotation of the crank rod 40 rotates the worm 42 that, in turn, rotates the worm gear 44 and spur gear 48, thereby moving the gear rack 38 either up or down depending on the direction of rotation of the crank shaft 40. The worm 42 and worm gear 44 hold the gear rack 38 in its desired position without the need for a further mechanical lock. The gear box 36 is securable on the guide rods 32, 34 by means of a locking bar 50 and lock screw 52 that is threaded into the locking bar 50. The locking bar 50 is also mounted on the guide rods 32, 34 and, as shown in FIG. 4, is mounted in a slot 54 of the gear box housing 36. With the lock screw 52 in the position illustrated in FIGS. 3 and 4, the gear box 36 is free to be moved over the length of the guide rods 32, 34. However, rotation of the lock screw 52 in a direction advancing the lock screw 52 through the locking bar 50, results in the lock screw 52 contacting the bottom surface 56 of the slot 54. Further, rotation of the lock screw 52 in the same direction pushes the locking bar 50 outward, that is, to the right, as illustrated in FIG. 4, thereby pressing the locking bar 50 tightly against the guide rods 32, 34 and securing the gear box 36 in a desired position with respect thereto.

Figure 5:
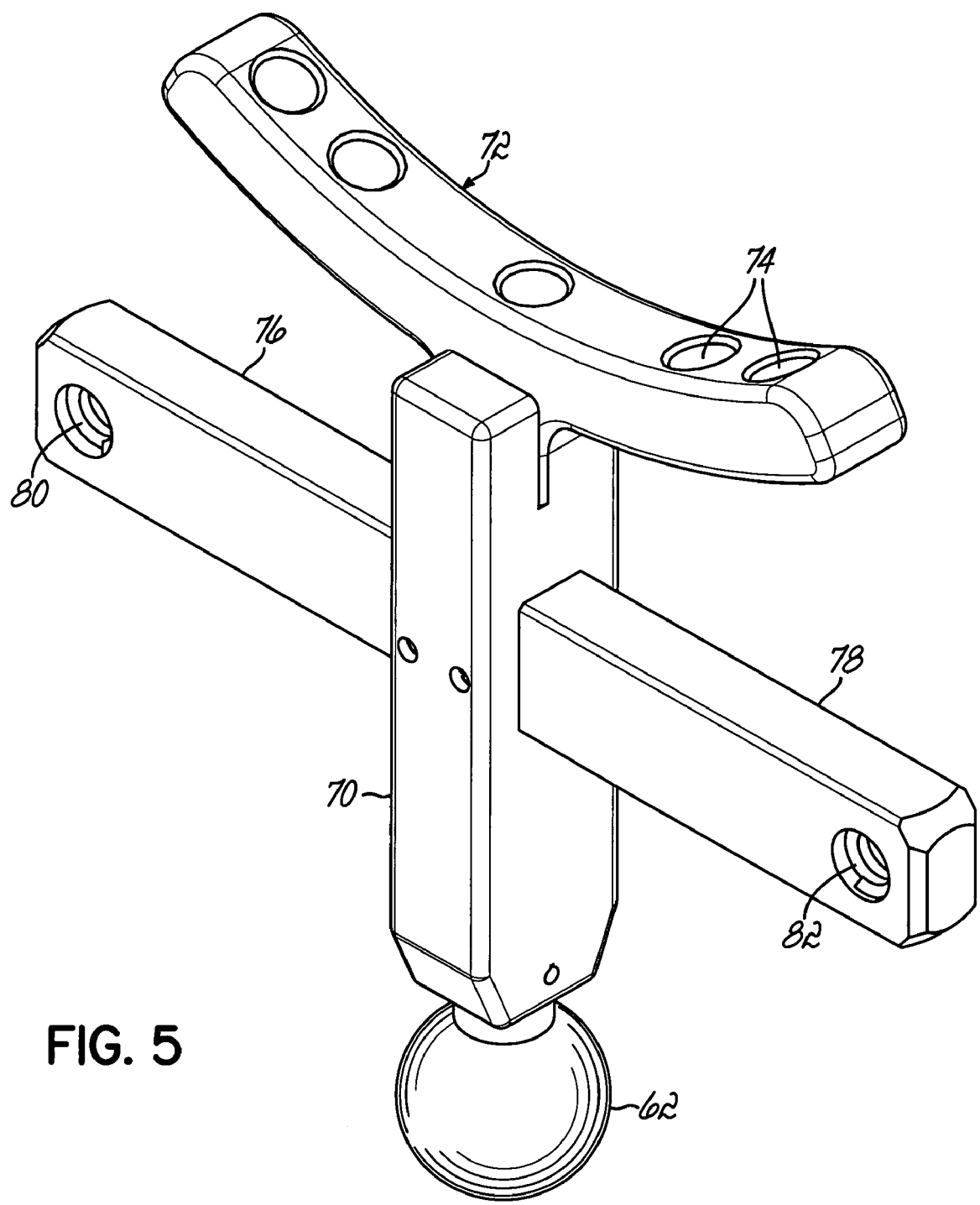
FIG. 5 is a perspective view of a rocker head support used with the head support system of FIG. 1.

The posts 24, 26, guide rods 32, 34, gear box 36 and gear rack 38 function as a support structure for head support and stabilization devices as will be subsequently described. Referring back to FIG. 2, a cage 56 is fixed to an upper end of the rack 38 and contains a socket 60 having a split 61. The socket 60 is pinned in the cage 56 and is sized slightly smaller than a ball 62. The split 61 spreads to permit the ball 62 to snap into an annular concave surface 63 of the socket 60, thereby forming a ball and socket joint 58. A locking screw 64 extends through the cage 56 and a clearance hole in a first end 66 of the socket 60. The locking screw 64 is threaded into an opposite end 68 of the socket 60. With the locking screw 64 loosened, the ball 62 is freely pivotable with respect to the socket 60 and can be locked at any desired orientation therewith by tightening the locking screw 64. As shown in FIG. 5, the ball 62 is fixed to a lower end of a support column 70. A rocker arm 72 is rotatably mounted on a pin (not shown) having its ends secured at an upper end of the support column 70, thereby permitting the rocker arm 72 to pivot through a small angle, for example, of about 30 degrees. The rocker arm 72 contains a plurality of holes 74 into which pins or pads can be mounted to provide a desired support of the occiput portion of the patient's head. The plurality of holes 74 permit the pins or pads to be mounted at different locations on the rocker arm 72. Alternatively, as will be appreciated, the rocker arm 72 can be rigidly fastened to the upper end of the support column 70.

Extending laterally from each side of the support column 70 is one of a pair of mounting brackets 76, 78. The mounting brackets 76, 78 have respective threaded holes 80, 82 for receiving mounting screws 84a, 84b (FIG. 1) of articulated arms 86a, 86b. The size and shape of the brackets 76, 78 and the number and location of respective mounting holes 80, 82 will change depending on the type of device being connected to the brackets 76, 78. The mounting brackets 76, 78 have respective threaded holes 80, 82 for receiving mounting screws 84a, 84b (FIG. 1) of articulated arms 86a, 86b. As shown in FIG. 1, the articulated arms 86a, 86b have lower ball and socket joints 88a, 88b, 90a, 90b that are substantially identical in construction to the previously described ball and socket joint 58. Lower ends of first arm 92a, 92b are fixed to respective sockets 90a, 90b; and second balls 94a, 94b are fixed to upper ends of respective first arms 92a, 92b. The second balls 94a, 94b are disposed in respective second sockets 96a, 96b to form second ball and socket joints substantially identical in construction to the ball and socket joint 58 previously described. Second arms 98a, 98b are rigidly attached to respective second sockets 96a, 96b. The sockets 96a, 96b are split and have respective locking screws 102a, 102b that are used to release and secure the respective first and second arms 92a, 92b and 98a, 98b at desired orientations.

Mounting posts 104a, 104b are frictionally secured within distal ends of the second arms 98a, 98b, respectively. Pads 106a, 106b are pivotally mounted to respective bases 107a, 107b in a known manner; and the bases 107a, 107b are attached to lower ends of the mounting posts 104a, 104b, respectively. Further in FIG. 1, occiput pads 108a, 108b are pivotally mounted to respective bases (not shown), that, in turn, are attached to the rocker arm 72. Thus, the occiput pads 108a, 108b support an occiput portion of the patient's head, and the pads 106a, 106b help stabilize the patient's head. The pivoting motion of the pads 106a, 106b, 108a, 108b permit them to be adjusted for optimum patient comfort and support.

Figure 6:
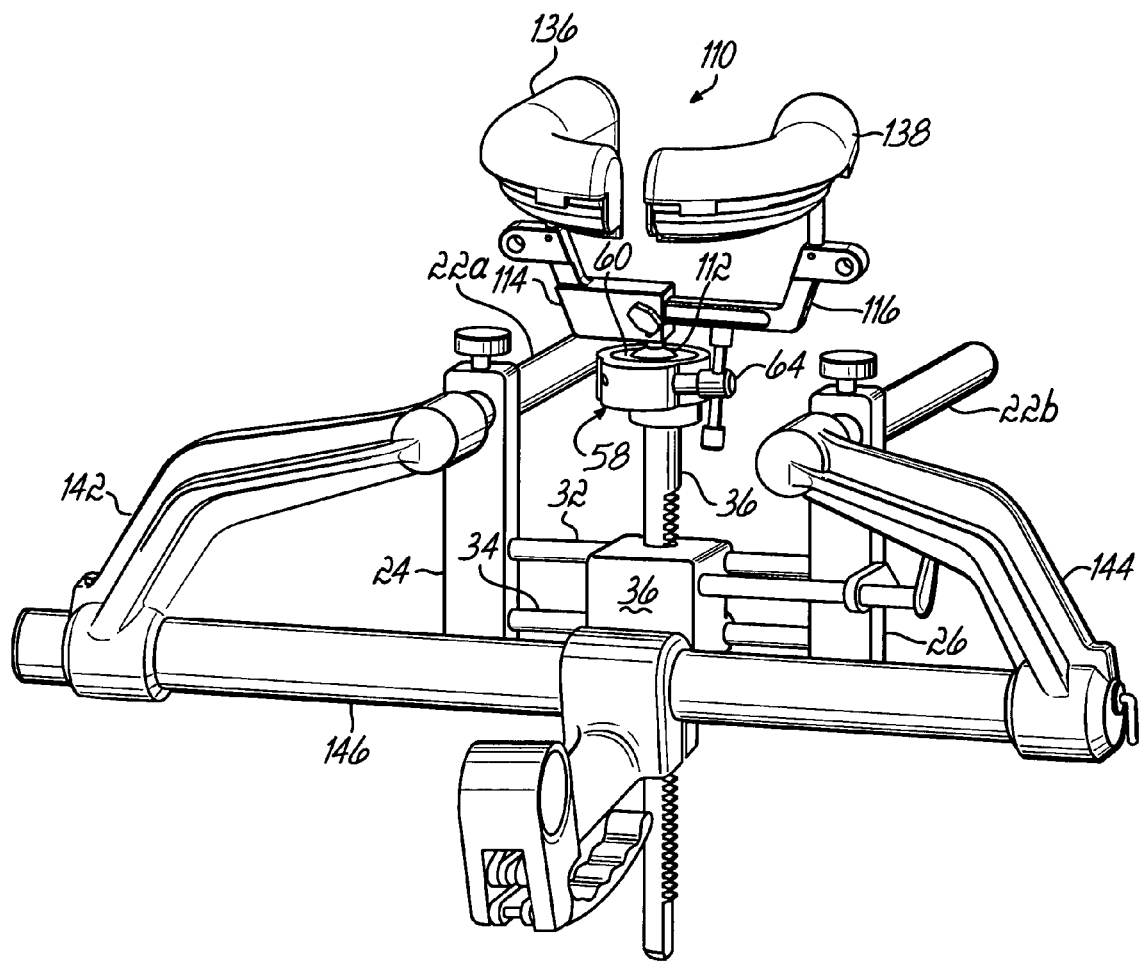
FIG. 6 is a perspective view of a second embodiment of a head support system in accordance with the principles of the present invention.
Figure 7:
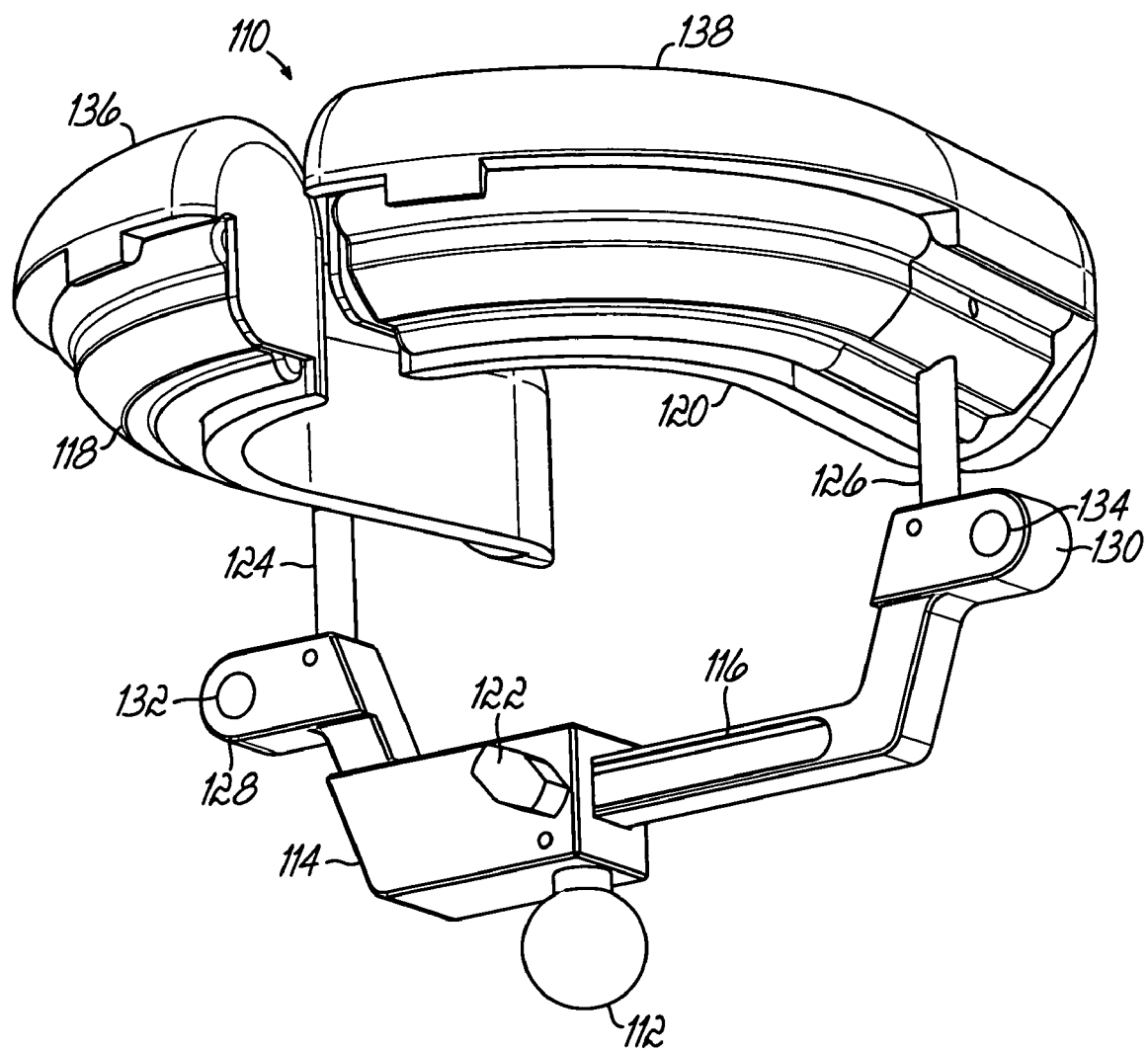
FIG. 7 is a perspective view of a horseshoe post assembly used with the head support system of FIG. 6.

A second embodiment of the head support 20 is shown in FIGS. 6 and 7, wherein components identical to the components shown in, and described with respect to, FIGS. 1 and 2 are identically numbered. The support 70, rocker arm 72 and occiput pads 108 of FIG. 1 are replaced by a horseshoe support 110 having pads 136, 138 for supporting a patient's head. A ball 112 is attached to a fixed horseshoe bracket 114 and is sized to snap into the socket 60 to form a ball and socket joint identical to the ball and socket joint 58 previously described. Thus, the horseshoe support 110 is pivotable with respect to the socket 60 and can be locked at any desired orientation by tightening the locking screw 64.

Referring to FIG. 7, a horseshoe slide arm 116 is slidable within the fixed horseshoe bracket 114. Thus, the spacing or distance between left and right horseshoe arms 118, 120 can be adjusted. A locking screw 122 is threaded through the fixed horseshoe bracket 114 and can be brought to bear against the slide arm 116, thereby securing the slide arm 116 and the right horseshoe arm 120 at a desired location with respect to the left horseshoe arm 118. The left and right horseshoe arms 118, 120 are fixed on the upper ends of respective mounting posts 124, 126. The lower ends of the mounting posts 124, 126 are fixed in the horseshoe bracket 114 and slide arm 116, respectively. Mounting blocks 128, 130 have respective threaded holes 132, 134 that receive screws (not shown), so that head stabilization devices, for example, articulated arms, etc., can be mounted to the horseshoe support 110. The horseshoe pads 136, 138 are mounted to the respective horseshoe arms 118, 120 in a known manner.

Figure 8:
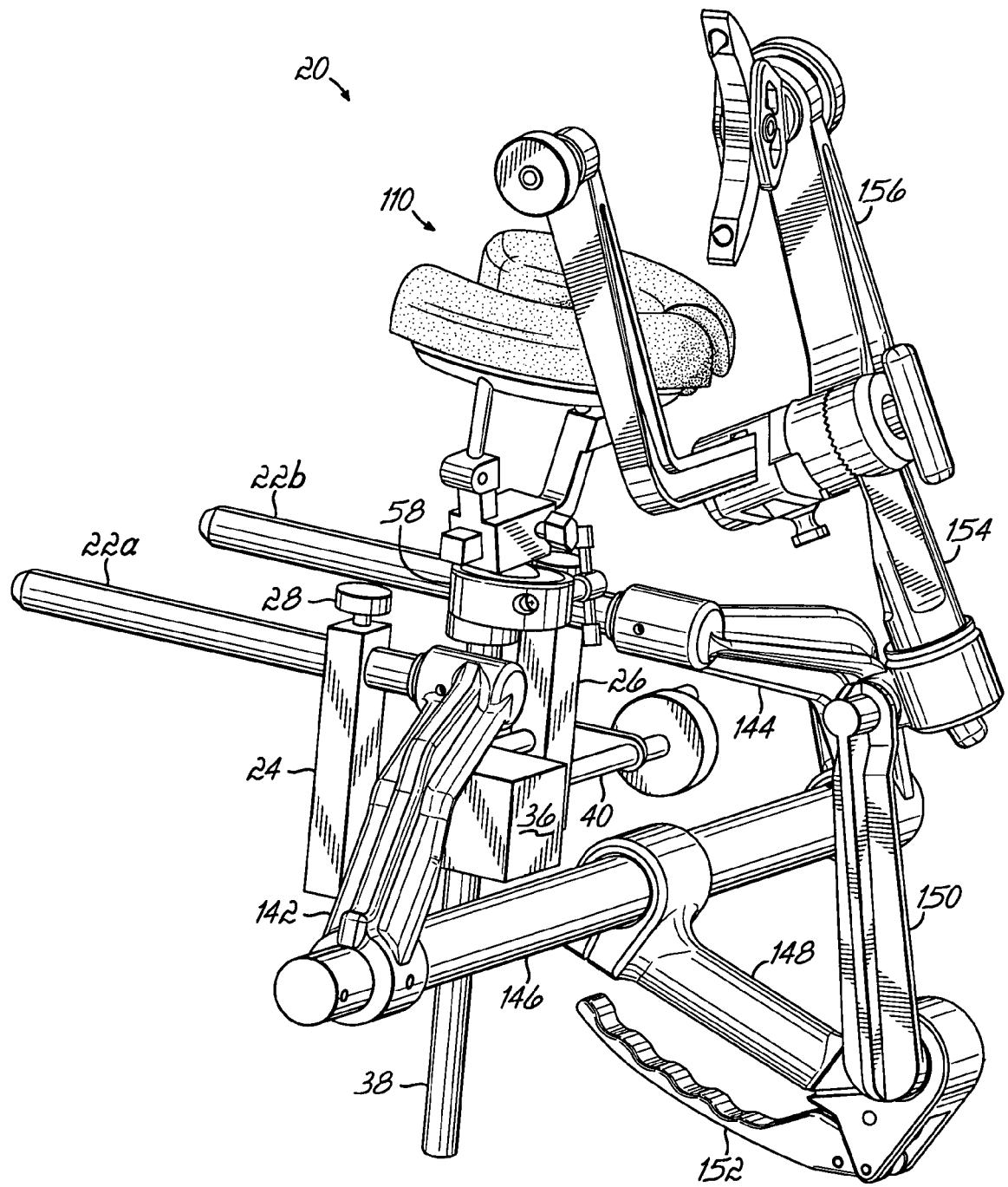
FIG. 8 is a perspective view of a third embodiment of a head support system in accordance with the principles of the present invention.

FIG. 8 illustrates a further embodiment of the head support system 20, wherein components identical to the components shown in, and described with respect to, FIGS. 1 and 2 are identically numbered. Brackets 142, 144 are connected to outer ends of respective support shafts 22a, 22b and a crossbar 146 is supported by the brackets 142, 144 in a known manner. One end of a base unit handle 148 is mounted on the crossbar 146, and the base unit handle 148 supports a transitional arm 150 at its opposite end. The base unit handle 148 is simultaneously made pivotable with respect to the crossbar 146 and the transitional arm 150 by releasing a closing handle 152 in a known manner. Securing the closing handle 152 simultaneously locks the orientation of the base unit handle 148 with respect to the crossbar 146 and transitional arm 150. A swivel adaptor 154 has a lower end releasably fixed to an upper end of the transitional arm 150, and a skull clamp 156 is releasably mounted to an upper end of the swivel adaptor 154 in a known manner.

Figure 9:
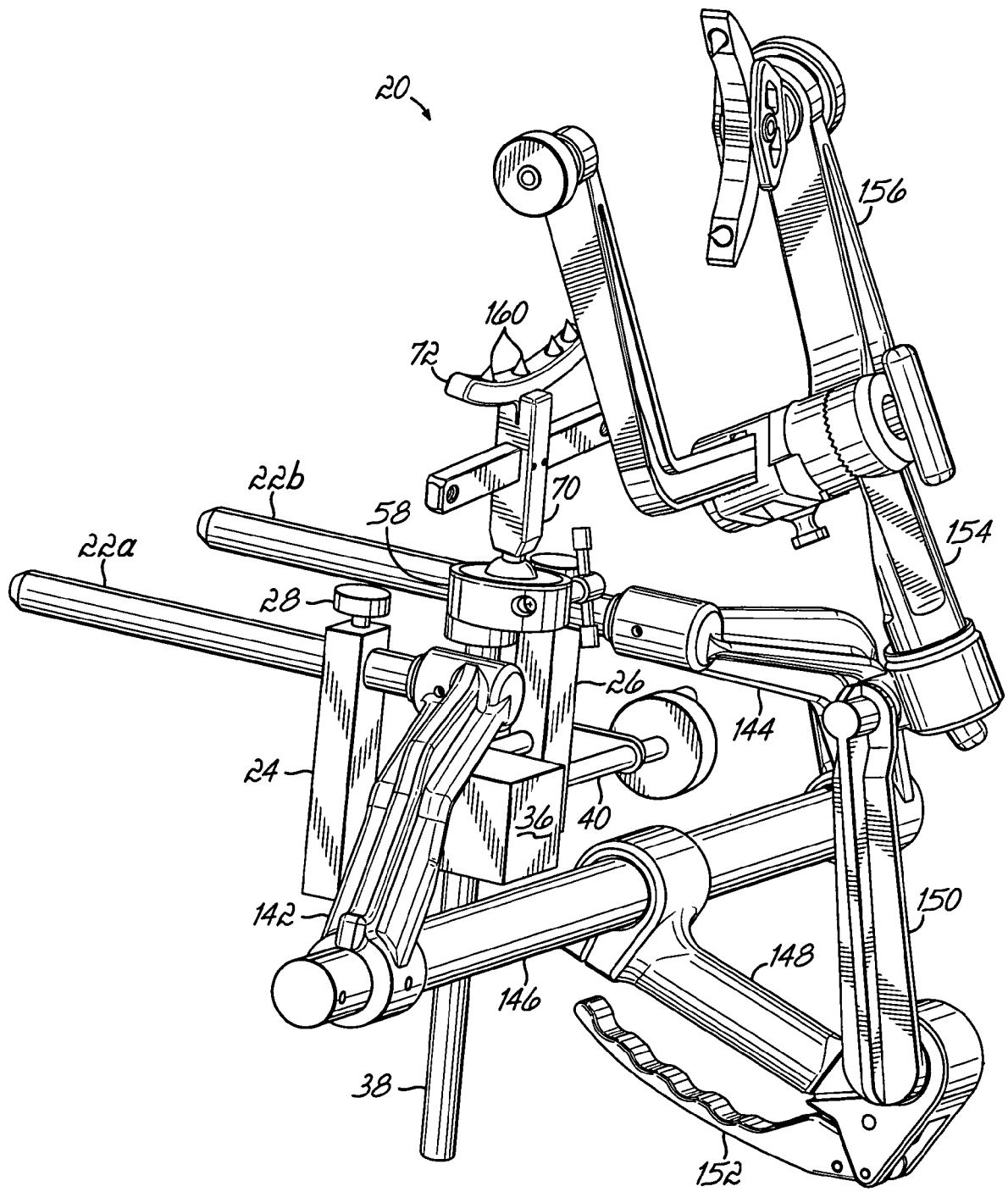
FIG. 9 is a perspective view of a fourth embodiment of a head support system in accordance with the principles of the present invention.

FIG. 9 illustrates a still further embodiment of the head support system 20, wherein components identical to the components shown in, and described with respect to, FIGS. 1 and 2 are identically numbered. In FIG. 9, the horseshoe support 110 of FIG. 8 is removed and replaced by the support column 70 and rocker arm 72 previously described with respect to FIGS. 1 and 5. However, the occiput pads 108 of FIG. 1 are replaced by skull pins 160 (FIG. 9) that are mounted at desired locations in holes 74 (FIG. 5) of the rocker arm 72 to support the patient's head.

In use, referring to FIGS. 1, 6, 8 and 9, prior to surgery, the head support 110 is first adjusted to support the static load of the patient's head. Thereafter, the skull clamp 156 is applied to the patient to stabilize the patient's head. In the process of supporting and stabilizing the patient's head, surgical draping is applied to the patient and portions of the head support system 20 in a known manner. Depending on the surgery being performed, it may be required to lower the head support out of contact with the patient's head and subsequently, raise the head support back into contact with the patient's head. With the present invention, the length of the crankrod 40 places the crankrod end at an outer, lateral position, so that it is more accessible and can be reached with minimal disturbance of the surgical draping. Further, the crankrod can be rotated with one hand to lower or raise the head support pads 108; and its worm gear construction mechanically locks the head support at a desired elevation without requiring a separate locking pin or screw.

The head support systems illustrated and described in FIGS. 1–9 have the advantage of providing independent and flexible support structures for both a static head support using a horseshoe pad, other pads, pins, etc. and head stabilization, for example, a skull clamp or other device for stabilizing the skull during imaging, neuro-navigational and surgical procedures. The head support systems permit a head support to be adjusted and simultaneously locked at any elevation with a motion of only one hand. Such a combination of static load support and stabilization is especially useful when working with pediatric patients and in plastic surgery. Further, the components of the head support systems are easily disassembled for ease of cleaning.

While the present invention has been illustrated by a description of an embodiment, and while such embodiment has been described in considerable detail, there is no intention to restrict, or in any way limit, the scope of the appended claims to such detail. Additional advantages and modifications will readily appear to those skilled in the art. For example, in the described embodiment, the static head support is shown and described as being occiput pads, a horseshoe pad and pins; however, as will be appreciated in alternative embodiments, other head support devices, for example, a single pad, may be used. Further, as will be appreciated, the horseshoe arms 118, 120 and respective pads 136, 138 may be made to different sizes to accommodate different sizes of patient's heads.

Further, in an alternative embodiment, the vertical posts 24, 26 can be inverted when greater elevation is required. This is desirable when the support shafts 22a, 22b are mounted at a lower location on the patient support or table. In this situation, the gear rack 38 is removed from the gear box 36; and the gear box 36 is removed from the guide rods 32, 34. The support posts 24, 26 are pivoted to extend upward from respective support shafts 22a, 22b. The gear box is inverted and remounted on the guide rods 32, 34; and the gear rack 38 is then reinserted in the gear box. In addition, in an alternative embodiment, the two guide rods 32, 34 can be replaced by a single guide rod having a noncircular cross-section to prevent rotation of the gear box 36 thereon.

In the described embodiment, the skull clamp 156 is one example of a skull clamp design that is often used to stabilize a patient's head. Again, as will be appreciated, in alternative embodiments, other skull clamp designs, for example, a single piece skull clamp, are equally applicable to provide a desired stabilization function. Similarly, although two articulated arms are illustrated and described, in some applications, a single articulated arm 86 and corresponding pads 106 may be used to stabilize the patient's head. Further, as will be appreciated, the pads 106 on the end of the articulated arm 86 may have various alternative designs.

Therefore, the invention in its broadest aspects is not limited to the specific details shown and described. Consequently, departures may be made from the details described herein without departing from the spirit and scope of the claims which follow.

What is claimed is:

1. A head support system for use with a patient support and providing support and stabilization for a patient's head, the head support system comprising:
    a support structure comprising a crossbar extending transverse to the patient support, the support structure adapted to be connected to the patient support;
    a head support removably mountable to a portion of the support structure exclusive of the crossbar and adapted to provide a static support for the patient's head; and
    a head stabilization device removably mountable to the crossbar of the support structure and adapted to stabilize the patient's head.

2. The head support system of claim 1 wherein the head support comprises a pad.

3. The head support system of claim 2 wherein the head support comprises a plurality of pads.

4. The head support system of claim 2 wherein the head support comprises a horseshoe head support.

5. The head support system of claim 1 wherein the head stabilization device comprises a skull clamp.

6. The head support system of claim 1 further comprising a ball-and-socket joint connecting the head support to the support structure.

7. A head support system for use with a patient support and providing support and stabilization for a patient's head, the head support system comprising:
- a support structure adapted to be connected to the patient support;
- a gear box mounted on the support structure;
- a head support supported by the gear box, the gear box being movable to move the head support in a generally vertical direction;
- a crank rod connected to the gear box and being operable to move the head support to, and simultaneously lock the head support at, a desired vertical position;
- a gear rack connected to the gear box; and
- a ball-and-socket joint connecting the gear rack to the head support, the head support being pivotable with respect to the gear rack.

8. The head support system of claim 7 wherein the gear box further comprises:
- a worm connected to, and rotatable by, the crank rod;
- a worm gear engaged with, and rotating with, the worm; and
- a spur gear mounted for rotation with the worm gear and engaged with the gear rack.

9. The head support system of claim 8 wherein the support structure comprises a guide rod for supporting the gear box, the guide rod extending a transverse direction to a length of the patient support.

10. A head support system for use with a patient support and providing support and stabilization for a patient's head, the head support system comprising:
- a support structure adapted to be connected to the patient support;
- a gear box mounted on the support structure;
- a head support supported by the gear box, the gear box being movable to move the head support in a generally vertical direction;
- a crank rod connected to the gear box and being operable to move the head support to, and simultaneously lock the head support at, a desired vertical position; and
- a head stabilization device removably mountable to the support structure and adapted to stabilize the patient's head.

11. A head support system for use with a patient support and providing support and stabilization for a patient's head, the head support system comprising:
- a pair of support shafts adapted to be mounted to the patient support and extending substantially parallel with a length of the patient support;
- a head support removably mountable to the pair of support shafts and adapted to provide static support for a head of a patient;
- a crossbar removably mountable to the pair of support shafts; and
- a head stabilization device removably mountable to the crossbar and adapted to stabilize the head of the patient.

12. A head support system for use with a patient support and providing support and stabilization for a patient's head, the head support system comprising:
- a support shaft adapted to be mounted to the patient support and extending substantially parallel with a length of the patient support;
- a guide rod mounted to the support shaft and extending in a transverse direction to the length of the patient support;
- a gear box mounted on the guide rod;
- a ball-and-socket joint having a fixed portion and a movable portion;
- a gear rack mounted in the gear box and connected to the ball-and-socket joint;
- a head support connected to the ball-and-socket joint, the head support being movable with respect to the ball-and-socket joint and adapted to provide static support for a head of a patient;
- a crossbar removably mountable to the support shaft; and
- a head stabilization device removably mountable to the crossbar and adapted to stabilize the head of the patient.

13. The head support system of claim 12 wherein the support shaft comprises a pair of support shafts.

14. The head support system of claim 13 wherein the guide rod is mounted to be slidable with respect to the pair of support shafts.

15. The head support system of claim 14 wherein the guide rod comprises a pair of guide rods.

16. The head support system of claim 14 wherein the gear box is mounted on the guide rod.

17. The head support system of claim 12 wherein the head support comprises a plurality of pads.

18. The head support system of claim 17 wherein each of the plurality of pads is adjustably separable in the transverse direction.

19. The head support system of claim 18 wherein the pair of pads comprise a pair of adjustable horseshoe pads.

20. The head support system of claim 12 wherein the head stabilization device comprises a skull clamp.

21. A method of supporting a head of a patient comprising:
- providing a support structure removably connectable to an end of a patient support, the support structure comprising a crossbar extending transverse to a patient support, and the support structure supporting a head support exclusive of the crossbar and supporting a head stabilization device on the crossbar;
- statically supporting the head of the patient with the head support; and
- simultaneously stabilizing the head of the patient with the head stabilization device.

* * * * *